US007622298B2

(12) United States Patent
Neumann (10) Patent No.: US 7,622,298 B2
(45) Date of Patent: Nov. 24, 2009

(54) METHOD FOR CREATING PERFUSABLE MICROVESSEL SYSTEMS

(75) Inventor: Thomas Neumann, Seattle, WA (US)

(73) Assignee: Norits, Inc., Gig Harbor, WA (US)

( * ) Notice: Subject to any disclaimer, the term of this patent is extended or adjusted under 35 U.S.C. 154(b) by 299 days.

(21) Appl. No.: 11/388,920

(22) Filed: Mar. 24, 2006

(65) Prior Publication Data

US 2007/0224677 A1   Sep. 27, 2007

(51) Int. Cl.
*C12N 5/06* (2006.01)
(52) U.S. Cl. .................. 435/395; 435/325; 435/397; 435/1.1; 435/1.2; 623/1.1; 623/1.41
(58) Field of Classification Search .................. None
See application file for complete search history.

(56) References Cited

U.S. PATENT DOCUMENTS

| 4,878,908 | A | 11/1989 | Martin et al. |
| 5,804,366 | A | 9/1998 | Hu et al. |
| 6,503,273 | B1 | 1/2003 | McAllister et al. |
| 6,592,623 | B1 | 7/2003 | Bowin et al. |
| 6,642,019 | B1 | 11/2003 | Anderson et al. |
| 6,893,812 | B2 | 5/2005 | Woltering |
| 6,989,071 | B2 | 1/2006 | Kocur et al. |
| 2002/0150879 | A1 | 10/2002 | Woltering |
| 2002/0177121 | A1 | 11/2002 | Woltering et al. |
| 2003/0138945 | A1 | 7/2003 | McAllister et al. |
| 2003/0138950 | A1 | 7/2003 | McAllister et al. |
| 2003/0171053 | A1 | 9/2003 | Sanders |
| 2004/0044403 | A1 | 3/2004 | Bischoff et al. |
| 2006/0216320 | A1 | 9/2006 | Kitazono et al. |

OTHER PUBLICATIONS

L'Heureux et al, "A completely biological tissue-engineered human blood vessel" FASEB Journal, 1998, vol. 12, pp. 47-56.*
Chrobak, "Formation of perfused, functional microvascular tubes in vitro," Microvascular Research 71 (May 2006) 185-196.
Akhtar,N, Dickerson EB, Auerbach R. 2002. The sponge/Matrigel angiogenesis assay. Angiogenesis 5:75-80.
Algire GH, Chalkley HW, Legallais FY, Park HD. 1945. Vascular reactions of normal and malignant tissues in vivo. I. Vascular reactions of mice to wounds and to normal and neoplastic transplants. J Natl Cancer Inst 6:73-85.
Andrade SP, Machado RD, Teixeira AS, Belo AV, Tarso AM, Beraldo WT. 1997. Sponge-induced angiogenesis in mice and the pharmacological reactivity of the neovasculature quantitated by a fluorimetric method. Microvasc Res 54:253-261.

(Continued)

*Primary Examiner*—Allison M Ford
(74) *Attorney, Agent, or Firm*—Citadel Patent Law; George A Leone (57) ABSTRACT

Microvessel networks are produced in vitro from tissue-engineered parent vessels sprouting into a supporting matrix, as for example gels, of extracellular matrix proteins. The microvessel systems are integrated into devices that allow for controlled perfusion with fluids. The vessels may include cells from one cell type, for example, endothelial cells, or from combinations of two or more cell types.

18 Claims, 7 Drawing Sheets

OTHER PUBLICATIONS

Arthur WT, Vernon RB, Sage EH, Reed MJ. 1998. Growth factors reverse the impaired sprouting of microvessels from aged mice. Microvasc Res 55:260-270.

Ausprunk DH, Knighton DR, Folkman J. 1974. Differentiation of vascular endothelium in the chick chorioallantois: a structural and autoradiographic study. Dev Biol 38:237-248.

Clark ER, Clark EL. 1939. Microscopic observations on the growth of blood capillaries in the living mammal. Am J Anat 64:251-301.

Davis GE, Camarillo CW. 1996. An alpha 2 beta 1 integrin-dependent pinocytic mechanism involving intracellular vacuole formation and coalescence regulates capillary lumen and tube formation in three-dimensional collagen matrix. Exp Cell Res 224:39-51.

Elsdale T, Bard J. 1972. Collagen substrata for studies on cell behavior. J Cell Biol 54:626-637.

Feder J, Marasa JC, Olander JV. 1983. The formation of capillary-like tubes by calf aortic endothelial cells grown in vitro. J Cell Physiol 116:1-6.

Fishman JA, Ryan GB, Karnovsky MJ. 1975. Endothelial regeneration in the rat carotid artery and the significance of endothelial denudation in the pathogenesis of myointimal thickening. Lab Invest 32:339-351.

Folkman J, Haudenschild C. 1980. Angiogenesis in vitro. Nature 288:551-556.

Folkman J, Haudenschild CC, Zetter BR. 1979. Long-term culture of capillary endothelial cells. Proc Natl Acad Sci U S A 76:5217-5221.

Gimbrone MA, Jr. 1976. Culture of vascular endothelium. In: Prog Hemost Thromb. p. 1-28.

Gimbrone MA, Jr., Cotran RS, Folkman J. 1974a. Human vascular endothelial cells in culture. Growth and DNA synthesis. J Cell Biol 60:673-684.

Gimbrone MA, Jr., Cotran RS, Leapman SB, Folkman J. 1974b. Tumor growth and neovascularization: an experimental model using the rabbit cornea. J Natl Cancer Inst 52:413-427.

Greenblatt M, Shubi P. 1968. Tumor angiogenesis: transfilter diffusion studies in the hamster by the transparent chamber technique. J Natl Cancer Inst 41:111-124.

Hoying JB, Boswell CA, Williams SK. 1996. Angiogenic potential of microvessel fragments established in three-dimensional collagen gels. In Vitro Cell Dev Biol Anim 32:409-419.

Jaffe EA, Nachman RL, Becker CG, Minick CR. 1973. Culture of human endothelial cells derived from umbilical veins. Identification by morphologic and immunologic criteria. J Clin Invest 52:2745-2756.

Jozaki K, Marucha PT, Despins AW, Kreutzer DL. 1990. An in vitro model of cell migration: evaluation of vascular endothelial cell migration. Anal Biochem 190:39-47.

Koike T, Vernon RB, Gooden MD, Sadoun E, Reed MJ. 2003. Inhibited angiogenesis in aging: a role for TIMP-2. J Gerontol A Biol Sci Med Sci 58:B798-805.

Kubota Y, Kleinman HK, Martin GR, Lawley TJ. 1988. Role of laminin and basement membrane in the morphological differentiation of human endothelial cells into capillary-like structures. J Cell Biol 107:1589-1598.

Kuzuya M, Kinsella JL. 1994. Induction of endothelial cell differentiation in vitro by fibroblast-derived soluble factors. Exp Cell Res 215:310-318.

Maciag T, Kadish J, Wilkins L, Stemerman MB, Weinstein R. 1982. Organizational behavior of human umbilical vein endothelial cells. J Cell Biol 94:511-520.

Madri JA. 1982. Endothelial cell-matrix interactions in hemostasis. Prog Hemost Thromb 6:1-24.

Madri JA, Pratt BM. 1986. Endothelial cell-matrix interactions: in vitro models of angiogenesis. J Histochem Cytochem 34:85-91.

Madri JA, Pratt BM, Tucker AM. 1988. Phenotypic modulation of endothelial cells by transforming growth factor-beta depends upon the composition and organization of the extracellular matrix. J Cell Biol 106:1375-1384.

Madri JA, Stenn KS. 1982. Aortic endothelial cell migration. I. Matrix requirements and composition. Am J Pathol 106:180-186.

Manoussaki D, Lubkin SR, Vernon RB, Murray JD. 1996. A mechanical model for the formation of vascular networks in vitro. Acta Biotheor 44:271-282.

Marx M, Perlmutter RA, Madri JA. 1994. Modulation of platelet-derived growth factor receptor expression in microvascular endothelial cells during in vitro angiogenesis. J Clin Invest 93:131-139.

Merwin JR, Anderson JM, Kocher O, Van Itallie CM, Madri JA. 1990. Transforming growth factor beta 1 modulates extracellular matrix organization and cell-cell junctional complex formation during in vitro angiogenesis. J Cell Physiol 142:117-128.

Montesano R, Orci L. 1985. Tumor-promoting phorbol esters induce angiogenesis in vitro. Cell 42:469-477.

Montesano R, Orci L, Vassalli P. 1983. In vitro rapid organization of endothelial cells into capillary-like networks is promoted by collagen matrices. J Cell Biol 97:1648-1652.

Montesano R, Pepper MS, Orci L. 1993. Paracrine induction of angiogenesis in vitro by Swiss 3T3 fibroblasts. J Cell Sci 105 (Pt 4):1013-1024.

Mori M, Sadahira Y, Kawasaki S, Hayashi T, Notohara K, Awai M. 1988. Capillary growth from reversed rat aortic segments cultured in collagen gel. Acta Pathol Jpn 38:1503-1512.

Nehls V, Drenckhahn D. 1995. A novel, microcarrier-based in vitro assay for rapid and reliable quantification of three-dimensional cell migration and angiogenesis. Microvasc Res 50:311-322.

Nehls V, Herrmann R. 1996. The configuration of fibrin clots determines capillary morphogenesis and endothelial cell migration. Microvasc Res 51:347-364.

Neumann T, Nicholson BS, Sanders JE. 2003. Tissue engineering of perfused microvessels. Microvasc Res 66:59-67.

Nicosia RF, Bonanno E, Smith M, Yurchenco P. 1994a. Modulation of angiogenesis in vitro by laminin-entactin complex. Dev Biol 164:197-206.

Nicosia RF, Bonanno E, Villaschi S. 1992. Large-vessel endothelium switches to a microvascular phenotype during angiogenesis in collagen gel culture of rat aorta. Atherosclerosis 95:191-199.

Nicosia RF, Nicosia SV, Smith M. 1994b. Vascular endothelial growth factor, platelet-derived growth factor, and insulin-like growth factor-1 promote rat aortic angiogenesis in vitro. Am J Pathol 145:1023-1029.

Nicosia RF, Ottinetti A. 1990. Modulation of microvascular growth and morphogenesis by reconstituted basement membrane gel in three-dimensional cultures of rat aorta: a comparative study of angiogenesis in matrigel, collagen, fibrin, and plasma clot. In Vitro Cell Dev Biol 26:119-128.

Nicosia RF, Tchao R, Leighton J. 1982. Histotypic angiogenesis in vitro: light microscopic, ultrastructural, and radioautographic studies. In Vitro 18:538-549.

Nicosia RF, Tchao R, Leighton J. 1983. Angiogenesis-dependent tumor spread in reinforced fibrin clot culture. Cancer Res 43:2159-2166.

Nicosia RF, Tuszynski GP. 1994. Matrix-bound thrombospondin promotes angiogenesis in vitro. J Cell Biol 124:183-193.

Passaniti A, Taylor RM, Pili R, Guo Y, Long PV, Haney JA, Pauly RR, Grant DS, Martin GR. 1992. A simple, quantitative method for assessing angiogenesis and antiangiogenic agents using reconstituted basement membrane, heparin, and fibroblast growth factor. Lab Invest 67:519-528.

Pepper MS, Montesano R, Vassalli JD, Orci L. 1991. Chondrocytes inhibit endothelial sprout formation in vitro: evidence for involvement of a transforming growth factor-beta. J Cell Physiol 146:170-179.

Rosen EM, Meromsky L, Setter E, Vinter DW, Goldberg ID. 1990. Quantitation of cytokine-stimulated migration of endothelium and epithelium by a new assay using microcarrier beads. Exp Cell Res 186:22-31.

Sage EH, Vernon RB. 1994. Regulation of angiogenesis by extracellular matrix: the growth and the glue. J Hypertens Suppl 12:S145-152.

Vernon RB, Angello JC, Iruela-Arispe ML, Lane TF, Sage EH. 1992. Reorganization of basement membrane matrices by cellular traction promotes the formation of cellular networks in vitro. Lab Invest 66:536-547.

Vernon RB, Gooden MD. 2002. New technologies in vitro for analysis of cell movement on or within collagen gels. Matrix Biol 21:661-669.

Vernon RB, Lara SL, Drake CJ, Iruela-Arispe ML, Angello JC, Little CD, Wight TN, Sage EH. 1995. Organized type I collagen influences endothelial patterns during "spontaneous angiogenesis in vitro": planar cultures as models of vascular development. In Vitro Cell Dev Biol Anim 31:120-131.

Vernon RB, Sage EH. 1999. A novel, quantitative model for study of endothelial cell migration and sprout formation within three-dimensional collage matrices. Microvasc Res 57:118-133.

Villaschi S, Nicosia RF. 1993. Angiogenic role of endogenous basic fibroblast growth factor released by rat aorta after injury. Am J Pathol 143:181-190.

Neumann, Thomas, 2005, Grant Abstract, Grant No. 1 R21 HL081152-01 awarded by NIH National Heart, Lung, and Blood Institute.

Ratner, Buddy D., 2003, Grant Abstract, Grant No. 5R24HL064387-04 awarded by NIH National Heart, Lung, and Blood Institute.

Nicosia, R.F., Ottinetti, A., Growth of Microvessels in Serum-Free Matrix Culture of Rat Aorta, Laboratory Investigation, vol. 63, No. 1, p. 115-122, 1990.

Maniotis, A. J. et al., Vascular Channel Formation by Human Melanoma Cells in Vivo and in Vitro: Vasculogenic Mimicry, American Journal of Pathology, vol. 155, No. 3, p. 739-752, Sep. 1999.

Neumann, T. et al., Tissue Engineering of Skeletal Muscle Using Polymer Fiber Arrays, Tissue Engineering, vol. 9, No. 5, p. 995-1003, 2003.

Lin, A. Y. et al., Distinguishing Fibrovascular Septa From Vasculogenic Mimicry Patterns, Arch. Pathol. Lab. Med., vol. 129, p. 884-892, Jul. 2005.

* cited by examiner

METHOD FOR CREATING PERFUSABLE MICROVESSEL SYSTEMS

STATEMENT REGARDING FEDERALLY SPONSORED RESEARCH

This invention was made with government support under Grant No. 1 R21 HL081152-01 awarded by NIH National Heart, Lung, and Blood Institute. The government has certain rights in the invention.

FIELD OF THE INVENTION

The present invention relates to methods for the study of physiological and pathological vascular growth, and vascular growth in response to angiogenic or angiostatic factors.

BACKGROUND OF THE INVENTION

During normal processes of vascular growth (e.g., the menstrual cycle, placentation, changes in adiposity, wound repair, inflammation), the creation of new blood vessels is regulated and eventually ceases. Significantly, the deregulation of vascular growth is a critical element of pathology. For example, tumor growth, diabetic retinopathies, arthritis, and psoriasis involve excessive proliferation of blood vessels that contributes directly to the pathological state. In contrast, impairment of vascular growth, characteristic of aged individuals, compromises the healing of wounds and the revascularization of tissues rendered ischemic by trauma or disease. Therefore, an understanding of the mechanisms that direct the assembly new blood vessels, and the processes that start and stop vascular growth, are central to the development of strategies to control vascularization in disease.

During the growth of new blood vessels (angiogenesis), sprouts arise from endothelial cells that line the lumens of capillaries and postcapillary venules—the smallest branches of the vascular system. Angiogenesis is a complex, multi-step process. Although published studies of angiogenesis number in the many thousands, the cellular mechanisms that mediate and regulate angiogenic growth and morphogenesis are poorly understood.

The details of angiogenic sprouting are difficult to observe in "real-time" in vivo because of the opacity of most tissues. Tissue sections are difficult to reconstruct in 3D and do not communicate the dynamic nature of vascular growth. Moreover, the region near the tips of angiogenic sprouts—a critical area of control of vascular invasion and morphogenesis—is rarely found in tissue sections. In order to overcome the limitations of conventional histology, a variety of "models" of angiogenesis in vivo and in vitro have been developed.

Models of angiogenesis in vivo: To circumvent the opacity of living tissues, investigators have observed angiogenesis through "windows" in living animals that include the naturally transparent tails of amphibian larvae (Clark and Clark 1939), or specialized viewing chambers either implanted into rabbit ears (Clark and Clark 1939), mouse skin (Algire, Chalkley et al. 1945) and hamster cheek pouches (Greenblatt and Shubi 1968) or developed from rabbit corneal pockets (Gimbrone, Cotran et al. 1974) or chick chorioallantoic membranes (Ausprunk, Knighton et al. 1974). From these early largely descriptive studies came validation of the central paradigm of tumor-induced vascular chemotaxis and the corresponding discovery of diffusible, tumor-derived molecules that promote vascular growth, Newer assays of angiogenesis in vivo measure vascular ingrowth into polymeric sponges or plugs of gelled basement membrane proteins implanted subcutaneously into rodents (Passaniti, Taylor et al. 1992; Andrade, Machado et al. 1997; Akhtar, Dickerson et al. 2002; Koike, Vernon et al. 2003). For all of their elegance, approaches in vivo are made difficult by: (1) intra-species variation in angiogenic response from animal to animal; (2) the lack of translation of results from one species to another; (3) high costs of animal purchase and maintenance; (4) public disapproval of the use of animals for research purposes; and (5) complexities encountered in animal surgeries and in the visualization and evaluation of results.

Two-dimensional 2D models of angiogenesis in vitro: In an effort to understand the molecular mechanics of angiogenesis, endothelial cells isolated from large vessels were cultured in flat dishes until they formed confluent, pavement-like monolayers that simulated the endothelial linings of blood vessels (Jaffe, Nachman et al. 1973; Gimbrone 1976). Although useful as models of proliferative responses to endothelial injury in large blood vessels (Gimbrone, Cotran et al. 1974; Fishman, Ryan et al. 1975; Madri and Stenn 1982; Madri and Pratt 1986; Jozaki, Marucha et al. 1990; Rosen, Meromsky et al. 1990), monolayer cultures of endothelial cells on rigid substrata do not typically organize into capillary-like tubes in simulation of angiogenesis. In 1980, however following successful long-term culture of capillary endothelial cells (Folkman, Haudenschild et al. 1979), it was reported that 20-40 day cultures of bovine or human capillary endothelial cells developed a 2D cellular network on top of the confluent cellular monolayer, a process termed "angiogenesis in vitro" (Folkman and Haudenschild 1980). The endothelial cells of the network appeared as "tubes" with "lumens" filled with a fibrillar/amorphous material that was interpreted to be an endogenously-synthesized network of "mandrels" on which the cells organized. Later studies reported similar 2D network formation by endothelial cells from large vessels (Maciag, Kadish et al. 1982; Madri 1982; Feder, Marasa et al. 1983) and by endothelial cells seeded on top of malleable, hydrated gels of basement membrane proteins (e.g. Matrigel® gel)(Kubota, Kleinman et al. 1988).

Although 2D models of vascular development remain in use today (the Matrigel®-based assay (Kubota, Kleinman et al. 1988) is available commercially), such models lack the following 5 defining characteristics of true angiogenesis.

1. Invasion—Endothelial cells in 2D models form networks on top of extracellular matrix and show little propensity to burrow into the extracellular matrix (Vernon, Angello et al. 1992, Vernon, Lara et al. 1995).

2. Directionality—In 2D models, the networks of endothelial cells form in vitro more or less simultaneously throughout a field of pre-positioned cells, whereas angiogenesis in vivo involves the vectorial invasion of extracellular matrix by filamentous sprouts that arborize by multiple levels of branching.

3. Correct polarity—Although the 2D models make unicellular tubes that markedly resemble capillaries (Maciag, Kadish et al. 1982; Feder, Marasa et al. 1983; Sage and Vernon 1994), their polarity is "inside-out", that is, they deposit basement membrane material on their luminal surfaces and have their thrombogenic surfaces facing outward to the surrounding culture media (Maciag, Kadish et al. 1982; Feder, Marasa et al. 1983)—opposite to the situation in vivo.

4. Lumen formation—Evidence that 2D models generate endothelial cell (EC) tubes with patent lumens is weak. Typically, the endothelial cell tubes have "luminal" spaces that are filled with extracellular matrix (either exogenous or synthesized by the cells)(Maciag, Kadish et al. 1982; Madri 1982; Feder, Marasa et al. 1983; Sage and Vernon 1994; Vernon, Lara et al. 1995). Where present, patent lumens usually appear as slit-like or narrow cylindrical spaces bounded by thick walls of endothelial cell cytoplasm—quite different from the inflated, thin-walled endothelial cell tubes that typify capillaries in vivo.

5. Cell specificity—The cellular networks in 2D models are generated by mechanical processes that may be accomplished by non-EC cell types (Vernon, Angello et al. 1992; Vernon, Lara et al. 1995). Indeed, mathematical modeling has shown that any adherent cell type capable of applying tensile forces to malleable, 2D extracellular matrix (either synthesized endogenously or supplied (e.g., Matrigel® gel)) can generate networks under optimal conditions (Manoussaki, Lubkin et al. 1996).

Three-dimensional (3D) models of angiogenesis in vitro: The recognition that angiogenesis in vivo occurs within a 3D extracellular matrix has led to a variety of models in which sprouting is induced within 3D gels of extracellular matrix in vitro. In an early 3D model, endothelial cells dispersed within collagen gels (Montesano, Orci et al. 1983) formed networks of cords and tubes (Elsdale and Bard 1972). Although the endothelial cell tubes exhibited correct polarity, the characteristics of invasion and directionality were lacking (the endothelial cells were pre-embedded and evenly dispersed in the extracellular matrix). Nonetheless, this approach has proven useful in studies of lumen formation (Davis and Camarillo 1996) and of responses of endothelial cells to growth factors (Madri, Pratt et al. 1988; Merwin, Anderson et al. 1990; Kuzuya and Kinsella 1994; Marx, Perlmutter et al. 1994; Davis and Camarillo 1996).

In an alternative approach, 1 mm sections (rings) of rat aorta embedded in a 3D plasma clot generated branching, anastomosing tubes (Nicosia, Tchao et al. 1982). Sprouts from the aortic rings exhibited angiogenesis-like invasion and directionality in addition to polarity. Explant models utilizing aortic rings from rats or microvascular segments from mice have been used to study the influence of tumors, growth factors, various extracellular matrix supports, and conditions of aging on angiogenesis (Nicosia, Tchao et al. 1983; Mori, Sadahira et al. 1988, Nicosia and Ottinetti 1990; Nicosia, Bonanno et al. 1992, Villaschi and Nicosia 1993, Nicosia, Bonanno et al. 1994; Nicosia, Nicosia et al. 1994; Nicosia and Tuszynski 1994; Hoying, Boswell et al. 1996; Arthur, Vernon et al. 1998).

A variety of models exist that induce purified endothelial cells (as monolayers or aggregates) to sprout invasively into underlying or surrounding 3D extracellular matrix gels (Montesano and Orci 1985; Pepper, Montesano et al. 1991; Montesano, Pepper et al. 1993; Nehls and Drenckhahn 1959; Nehls and Herrmann 1996; Vernon and Sage 1999; Vernon and Gooden 2002). Each of these models has specific limitations that include difficulty in visualizing sprout formation, limited sprouting, a requirement for sectioning, or lack of effectiveness with certain types of endothelial cells.

Wolverine and Gulec have disclosed a 3D angiogenesis system (US 2002/0150879 A1) that involves embedding a fragment of tumor tissue into a matrix. The outgrowth of microvessels can be characterized to assay the angiogenic potential of the tissue. However, this approach does not provide luminal perfusion of the microvessels.

Neumann (the inventor here) et al. 2003, has disclosed the possibility of creating perfused microvessels in vitro that can be included in an artificial tissue. Neumann et al. 2003 teaches using 127 micrometer nylon fishing line as mandrels held by shrink tubing for making microvessels. The vessels were made from rat aortic smooth muscle cells embedded in agar. These microvessels were of an exploratory nature and not suitable for creating a human vessel graft.

Angiogenesis in vitro, a new approach: Two-dimensional models of vascular growth in vitro do not establish the defining characteristics of angiogenesis listed previously, whereas existing 3D models reproduce some or most of the characteristics. Importantly, none of the 3D models currently available reconstruct a parent blood vessel that contains a pressurized, flowing, circulatory fluid. Consequently, none of the existing in vitro 3D models permit study of the contribution of luminal pressure and flow to vascular growth and morphogenesis.

The present invention overcomes the limitations of existing models of angiogenesis by combining proven methods for generating invasive, tubular, microvascular sprouts in 3D extracellular matrix (ECM) with novel methodologies for the fabrication of an tissue-engineered parent vessel that will be the source of luminal flow. Via the perfusate, angiogenesis-modulatory compounds can be administered to the luminal surface of endothelial cells where specific target receptors are known to reside. The presence of a luminal flow of nutrient medium will substantially increase the survival time of capillary tubes in vitro. The disclosed angiogenesis system can be used evaluate a variety of experimental parameters that include hypoxia/hyperoxia, test of specific soluble bioactive compounds, use of genetically modified cells, and gene delivery via viral transfection. The system allows the study of angiogenesis relative to wound repair, aging, cancer, and atherosclerosis. Importantly, a model following the teachings of the present invention may be adapted to provide fully functional vascular systems capable of being incorporated into bioengineered artificial tissues.

The present invention also provides new and novel approaches, including a manifold design for making microvessels, making microvessels from endothelial cells and making larger vessels (e.g. having the size of coronary arteries). These and other important new teachings, including, for example, a method for creation of microvascular networks are evident from the specification and claims hereinbelow.

SUMMARY OF THE INVENTION

A method for creating networks of perfusable microvessels in vitro, said method comprising the steps of:

creating at least one parent vessel by culturing cells onto and around a set of mandrels;

embedding the at least one parent vessel into a matrix;

inducing the at least one parent vessel the at least one parent vessel to create sprouts in the matrix;

extracting the set of mandrels; and subjecting the at least one parent vessel and sprouts to luminal perfusion to imitate natural blood flow from the arterial end to the venous end of the capillary bed so as to create a microvessel network.

DETAILED DESCRIPTION OF THE PREFERRED EMBODIMENTS

The examples presented herein are for the purpose of furthering an understanding of the invention. The examples are illustrative and the invention is not limited to the example embodiments. The method of the present invention is useful for the study of physiological and pathological vascular growth, and vascular growth in response to angiogenic or angiostatic factors. Other useful applications are to methods that evaluate the angiogenic potential of cancer tissues and the response to antiangiogenic drugs. Additionally, the method of the invention may be used to construct various wound-healing devices and for vascularization of tissue-engineered constructs.

In one example a method and device for the creation of perfusable three-dimensional microvessel networks is disclosed. As used herein "EC" refers to endothelial cells, "SMC" refers to smooth muscle cells and "CAS" refers to coronary-artery substitutes.

Figure 1A:
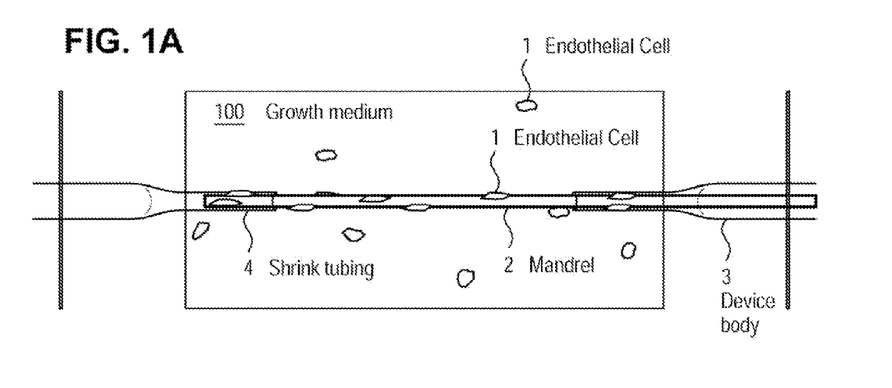
FIG. 1A, FIG. 1B and FIG. 1C schematically show an example of parent-vessel creation employed in accordance with the method of the invention.
Figure 1B:
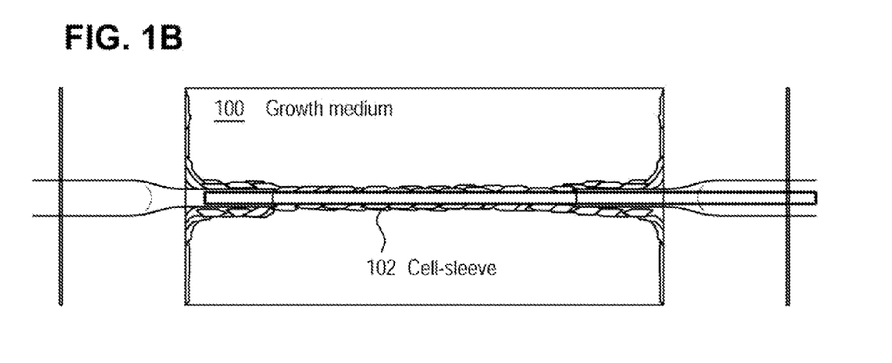
Figure 1C:
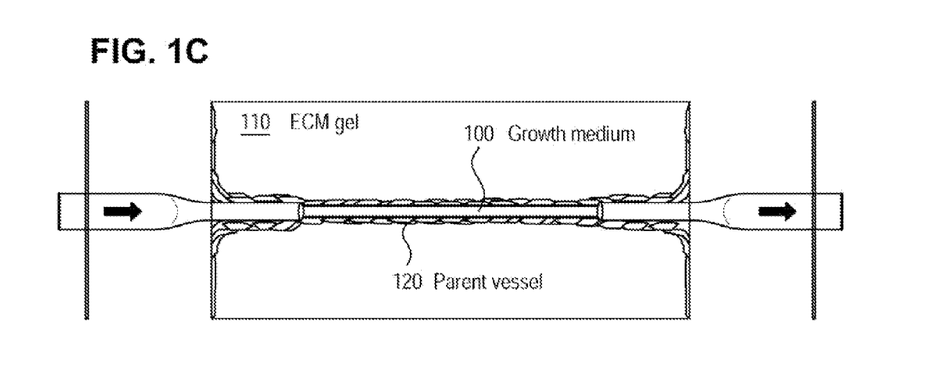

Generally, the devices for the culture and perfusion of microvessel networks consist of a chamber holding one or more mandrels in the center (as best shown in FIG. 1). The chambers can be fabricated from any biocompatible material and by a number of techniques, for example, by sandwiching laser-cut frames. The mandrels are assembled within the chamber in such way that they are retractable. This can be achieved by fitting the ends of the mandrels into tubing, as for example, by heat shrinking, (as demonstrated in FIG. 2). The diameter of the mandrels depends on the desired vessel caliber. The setup can be modified to accommodate single vessels, two vessels, or up entire arrays of vessels in 2D or 3D. Mandrels can be of various materials, such as polymer fibers, glass fibers, wires or the like.

Microvessels are created by seeding cells onto the mandrels, stimulating the cells to multiply around the mandrels, and extracting the mandrels when cells have formed vessel walls. The vessels are then embedded in a matrix. Depending on the culture conditions, the composition of the matrix, and the presence of angiogenic stimuli (e.g. growth factors), the parent vessels will sprout into the surrounding matrix. The sprouts will anastomoze with each other and, thus leading to the formation of capillary networks. After removal of the mandrels, the devices are connected to a perfusion system, and vessels are subjected to luminal fluid flow.

Referring now to FIG. 1A, FIG. 1B and FIG. 1C, there shown is an example schematic of parent-vessel creation employed by the method of the invention FIG. 1A shows endothelial cells 1 in a culture growth medium 100, seeded onto mandrel 2 held by shrink tubing 4 in a device body 3. FIG. 1B shows that the cells 1 have multiplied and formed a circular layer in the form of cell-sleeve 102. FIG. 10 shows the cell-sleeve after extraction of the mandrel 2 in an extracellular matrix (ECM) gel 110 being perfused with culture growth medium 100. The invention comprises the engineering of perfusable bioartificial vessel structures for tissue-engineering applications and research models. The general principle of the invention involves the culture of cells in layers around removable mandrels that are tightly fit into thin-wall tubing or other fittings. Once the cell layers have reached a desired wall thickness, the mandrels are removed, and the hereby-created bioartificial vessels (BAVs) may be perfused with culture medium, blood, blood substitutes, or other fluids by aid of a perfusion system. The method of the present invention allows for the production of mass manufactured or custom-created blood vessels, perfused in vitro angiogenesis models, wound healing devices, tissue components, whole tissues and organs, as well as research models.

Manufacture of Culture/Perfusion Devices

Referring now to FIG. 2A, FIG. 2B, FIG. 2C and FIG. 2D there shown is an example schematic of a known heat-shrink process used in one embodiment of the method of the invention. As shown specifically in FIG. 2A each culture/perfusion device (CPD) may comprise one or more mandrels 2 held by a supporting frame 12. The mandrels 2 of the diameter of the desired vessel caliber are fit with their ends tightly into medical-grade shrink tubing segments 4. The mandrels 2 may comprise biocompatible fibers (e.g. polymer, glass), wires or equivalents having diameters from several micrometers up to several millimeters depending on the vessel size being emulated.

Figure 2A:
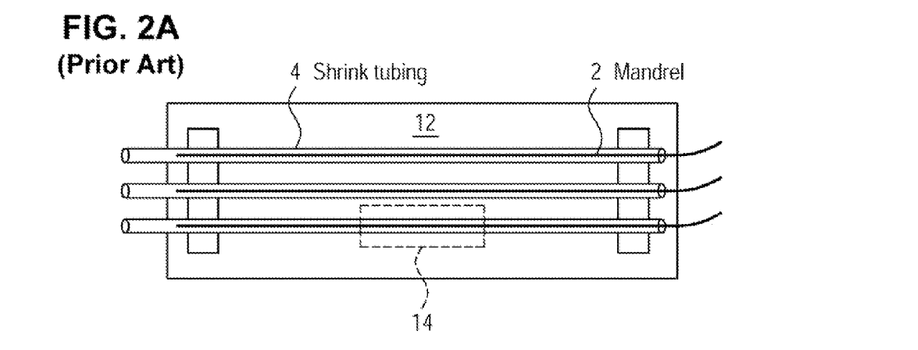
FIG. 2A, FIG. 2B, FIG. 2C and FIG. 2D schematically show an example of a known heat-shrink process employed in accordance with the method of the invention.
Figure 2B:
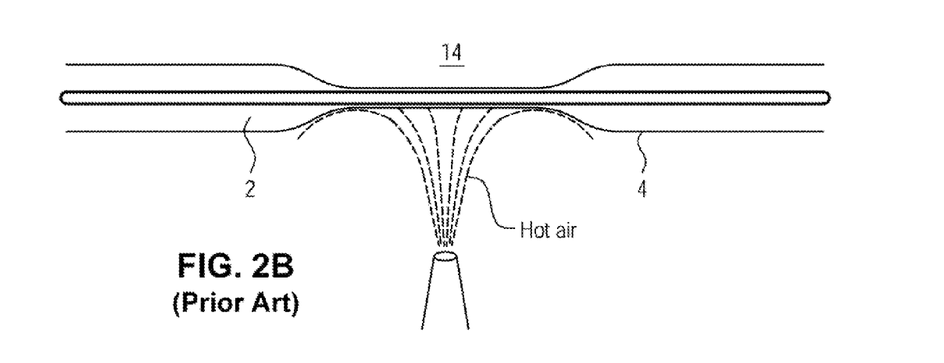
Figure 2C:
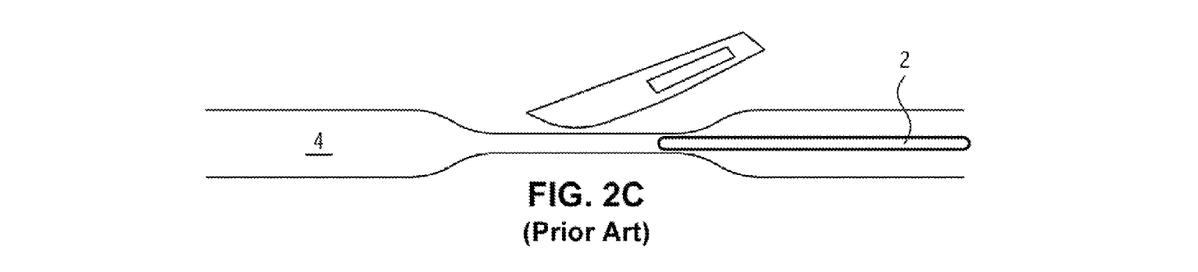
Figure 2D:
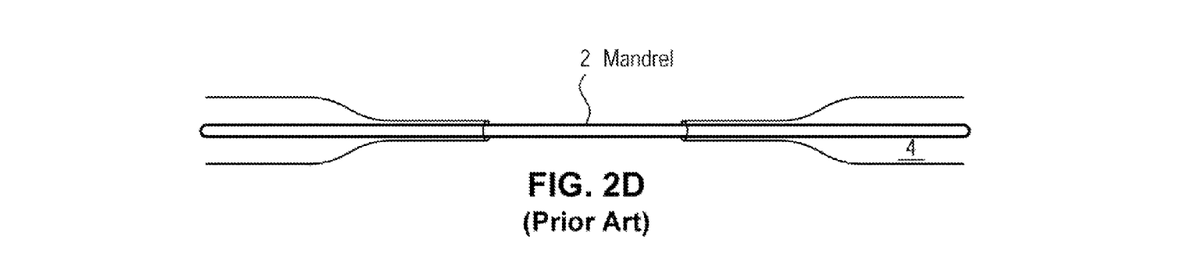

As shown in the more detailed drawing of FIG. 2B a central portion 14 of each shrink tubing segment 4 is heat-shrunk around one of the mandrels 2. Subsequently, as specifically shown in FIG. 2C, the mandrel 2 is retracted, and the tubing cut. FIG. 2D shows the situation after re-positioning the mandrel such that both ends of the mandrel are enclosed by the now cut-and-separated shrink tubing segment 4. The frames 12 may be fabricated using various materials and techniques. The setup may be modified to accommodate either single bioartificial vessels or arrays of bioartificial vessels. Similarly, by layering several planes of mandrel arrays, a thick, perfusable tissue may be generated with vascular networks.

Machining of Perfusion Chambers

Figure 3A:
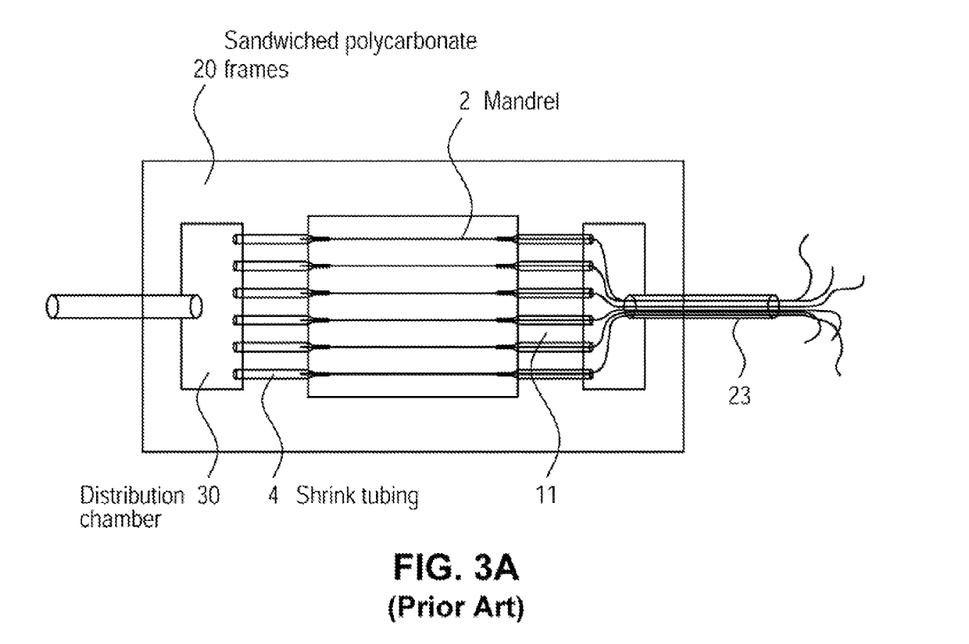
FIG. 3A schematically shows a known design for mounting culture/perfusion devices employed in accordance with the method of the invention.

Referring now to FIG. 3A a known setup for the perfusion of several mandrel/shrink-tubing assemblies 11 is shown. A frame 20 may advantageously be milled from polycarbonate or equivalent materials. Distribution chambers 30 may be included into the design, which allows for simultaneous perfusion of many bioartificial vessels. Ends of a set of threads comprising the mandrels 2 are gathered in a silicon tube 23.

Laser Cutting of Mylar Frames

Figure 3B:
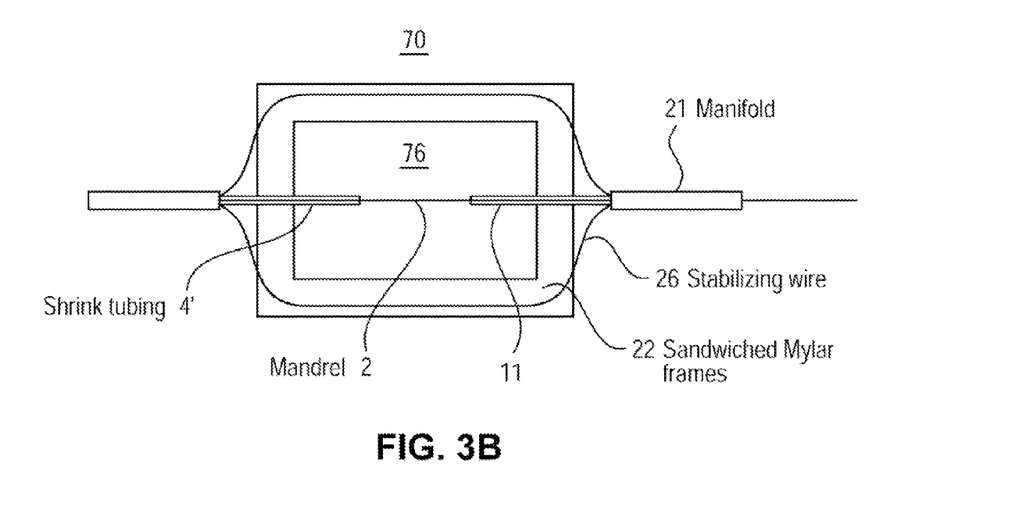
FIG. 3B schematically shows a design used in a manufacturing method for mounting culture/perfusion devices employed in accordance with the method of the invention.

Referring now to FIG. 3B a novel design used in a manufacturing method for mounting culture/perfusion devices employed in accordance with the method of the invention is schematically shown. A single vessel design, CPD 70, may advantageously be created by sandwiching a mandrel 2 held by heat-shrink tubing 4 between two laser-cut Mylar® frames 22. A cylindrical epoxy manifold 21, constructed as detailed below, may advantageously be used for holding the mandrel/shrink-tubing assembly 11.

Mandrel/shrink-tubing assemblies may be sandwiched between two frames of a polyester film or the like, such as Mylar®, with adhesive sides pressed together such that each mandrel is suspended in the frame window 76 by two shrink-tubing segments 4' at each end. The two shrink-lubing segments 4' are stabilized and strengthened by inclusion of at least one thin stabilizing wire 26 in the frame 22 and by encapsulation in cylindrical epoxy manifolds that are cast around the shrink-tubing and the at least one thin stabilizing wire 26 by use of a mold of silicone tubing. The two shrink-tubing segments 4' will eventually become the inflow and outflow ports for the CPD 70.

Figure 4A:
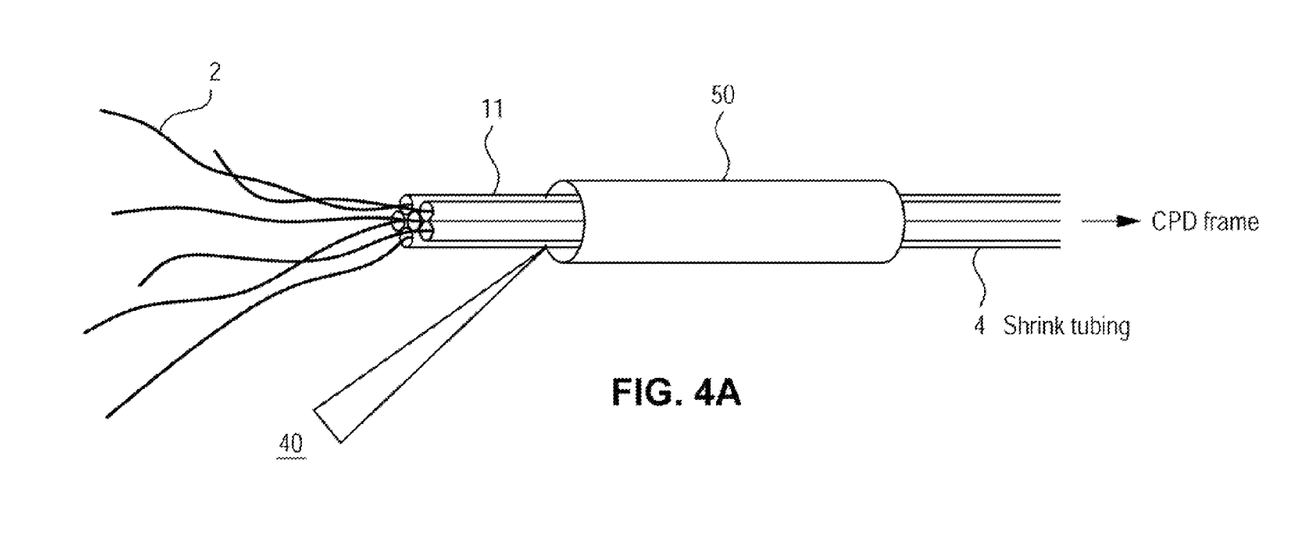
FIG. 4A and FIG. 4B schematically show creation of manifolds for culture/perfusion devices employed in accordance with the method of the invention.
Figure 4B:
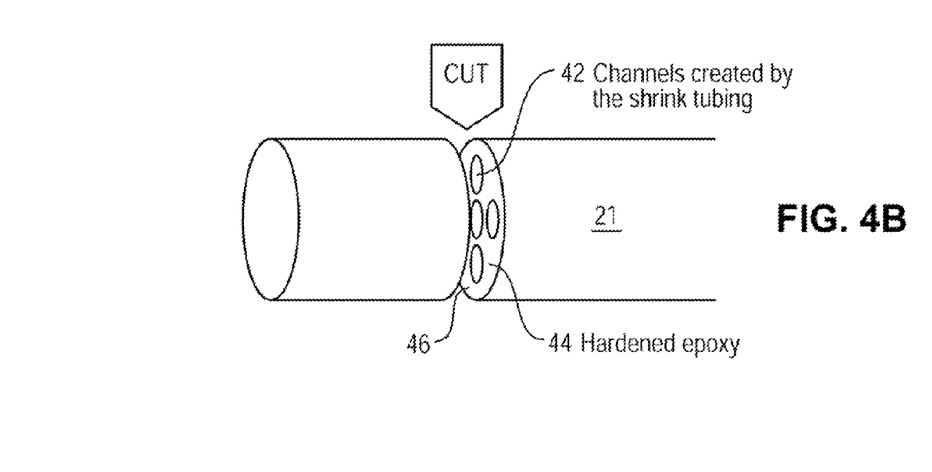

Referring now to FIG. 4A and FIG. 4B, there schematically shown is a method for creation of manifolds for the devices in accordance with the method of the invention. FIG. 4A particularly shows a plurality of shrink-tubing/mandrel assemblies 11 pulled through a sleeve of, for example, silicone tubing 50. An epoxy glue 40 is injected to fill the silicone tubing 50 and allowed to harden.

FIG. 4B particularly shows the condition after the epoxy glue 40 has hardened and the silicone tubing 50 is slit open and removed. Remaining is a hardened epoxy rod 44. The epoxy rod 44 is cut after the mandrels have been retracted behind the cutting spot leaving channels 42 created by the shrink tubing. The ends 46 of many shrink tubes may be integrated to form a manifold 21. Stacking of individual CPDs or CPD frame assemblies can be used to create 3D vessel arrays.

Alternative Methods

Figure 5A:
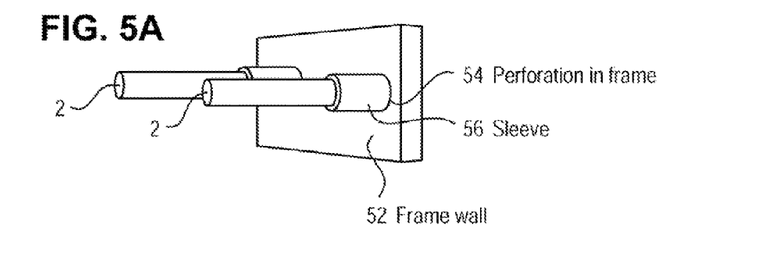
FIG. 5A, FIG. 5B and FIG. 5C schematically show an alternative design for microfabricated culture/perfusion devices constructed in accordance with the method of the invention.
Figure 5B:
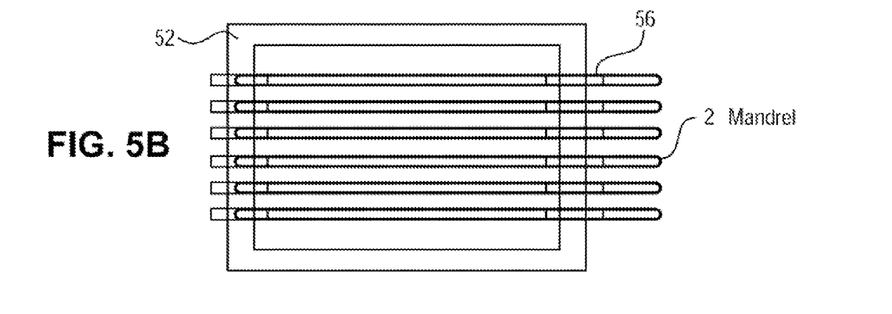
Figure 5C:
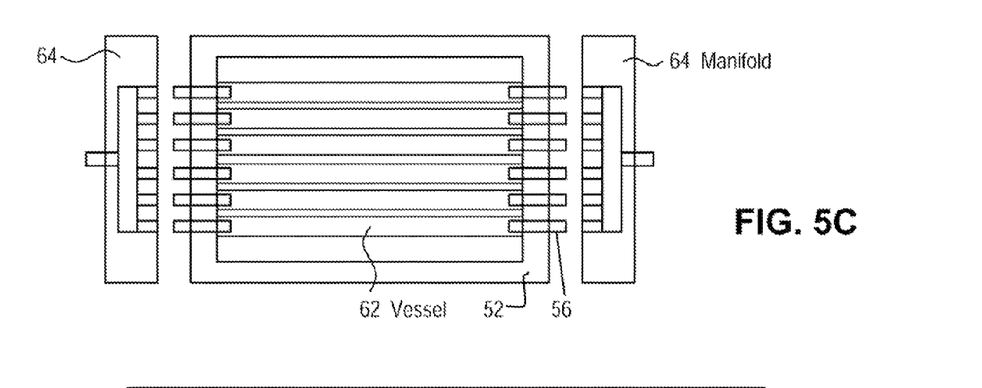

Referring now to FIG. 5A, FIG. 5B and FIG. 5C there schematically shown is an alternative design for microfabricated culture/perfusion devices in accordance with the method of the invention. FIG. 5A particularly shows a set of mandrels 2 introduced through small perforations 54 in a frame where the perforations have sleeves 56, which substitute for the shrink tubing. FIG. 5B particularly shows a CPD before cell seeding including a set of mandrels 2 mounted in a frame wall 52.

FIG. 5C particularly shows an alternate example of a culture/perfusion device with vessels 62 where microfabricated manifolds 64 may be attached to the sleeves 56 on the outside of the frame 52. The vessels 62 are grown on mandrels as shown herein and remain after the mandrels are removed. Microfabrication methods, such as micro molding, may be used for the mass production of such CPR frame assemblies.

Vessel Creation and Perfusion

Figure 6:
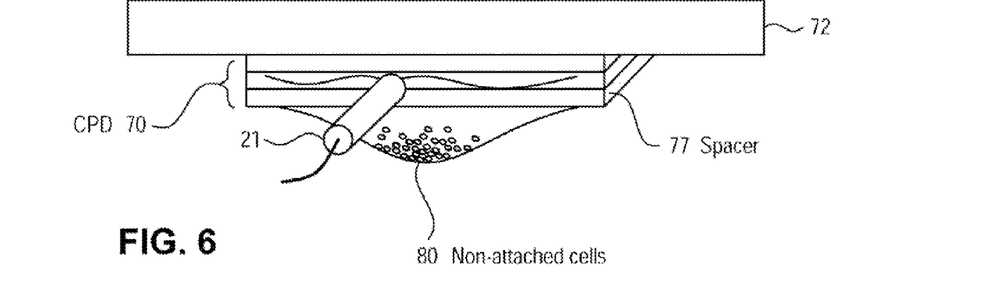
FIG. 6 schematically shows a cell-seeding procedure employed in accordance with the method of the invention.

Referring now to FIG. 6 there schematically shown is a cell-seeding procedure in accordance with the method of the invention. In order to prepare the CPDs 70 for cell seeding, they are first cleaned and then UV-sterilized. Under sterile conditions, the CPDs are fixed to a surface, e.g. the bottom of the Petri dish 72. The inner window 76 (as shown in FIG. 3B) of the CPD frame assembly 70 is then filled with a solution that contains an attachment-protein, such as laminin-1. One or more spacers 77 may be used as necessary. After an incubation period, the attachment-protein containing solution is removed, and a suspension of the desired cell type (e.g. smooth muscle cells or endothelial cells) in culture medium is then transferred into the window 76 of the CPD 70.

Cell seeding may be done by filling a volume of cell suspension into the window 76, and flipping the CPD frame assembly 70 upside down, thus creating a hanging droplet 80. During an incubation period of about 45 min., a large number of cells will attach to the mandrel/shrink tubing assemblies within the CPD frame assembly. Excessive cells will sink into the tip of the hanging drop and may be easily collected and discarded. The Petri dish, containing one or more CPD frame assemblies, is then returned into an upright position, filled with culture medium until the CPD frame assemblies are flooded, and incubated. The incubation conditions in one example were in an environment of 5% $CO_2$ at 37° C. The cells attached to the mandrel/shrink tubing assemblies will spread out and multiply, forming concentric monolayers (e.g. endothelial cells) or multilayers of 150 µm and more in thickness (e.g. smooth muscle cells).

At the desired wall configuration or thickness the mandrels are extracted, thereby creating hollow cellular tubes. Thinner walls may be protected from rupture by casting a gel such as, for example, agarose, collagen, a gel of basement membrane proteins or the like, around the cell sleeves prior to mandrel extraction. The manifolds of the CPD frame assemblies are then connected to a perfusion system and perfused with the fluid of choice, such as growth medium.

In another embodiment of the invention, a method for the creation of endothelial "parent" vessels from human vascular endothelial cells (HUVEC) comprises the steps wherein:

The culture device is first cleaned and then sterilized by UV exposure for 30 min. from each side. Under sterile conditions, the device is fixed to the bottom of a Petri dish with sterile strips.

The inner window of the device is then filled with an attachment-protein solution of laminin-1 (other attachment proteins, such as fibronectin, fibrin, or gelatin can be used instead).

After overnight incubation, the attachment-protein containing solution is removed, and a suspension of human vascular endothelial cells in culture medium is then transferred into the window of the device.

The Petri dish is then flipped upside down, thus creating a hanging drop of cell-medium suspension in the window of the device. After a 45 min. incubation period in a cell culture incubator (5% $CO_2$, 37° C.) a large number of cells will be attached to the mandrel/shrink tubing assemblies within the devices.

The Petri dish is then brought back into the upright position, and filled with growth medium for human vascular endothelial cells until the device is submerged.

Cells not bound to the mandrels will float off and can be aspirated and discarded.

The Petri dish is then placed in an incubator (5% $CO_2$; 37° C.). The cells attached to the mandrels will spread out and multiply, forming concentric monolayers of human vascular endothelial cells.

The culture medium is then removed from the Petri dish. A collagen solution is filled into the window of the culture device, and allowed to solidify, thus embedding the mandrel with the cell layer.

The human vascular endothelial cells will form sprouts into the collagen gel. The mandrel is then slowly extracted, leaving behind a perfusable "parent" microvessel of human vascular endothelial cells.

The manifolds of the device are then connected to a perfusion system and perfused with human vascular endothelial cells growth medium.

Perfusion System

The CPDs may be attached to perfusion systems either in linear or in circulatory mode. A linear setup may be created with a gravity flow system, or a commercially available or custom-built syringe pump. Syringes are filled with perfusion medium, mounted into the syringe pump and connected to the upstream ends of the CPDs via gas-tight tubing. The CPDs may be stored in an incubator under sterile conditions or a sterile cell culture environment may be established within the CPD. The downstream manifold of the CPDs are connected to end reservoirs that collect the perfusate. A circulatory system may be built by using a peristaltic pump. Both, the linear and the circulatory system may be fitted with devices for gas exchange. Gas concentration, perfusion pressure, flow, temperature, and the concentration of nutrients and metabolic byproducts are measured with sensors. The collected data may be fed into a feedback loop, allowing for tight control of the desired parameters.

Specific Applications

Models for Angiogenesis Related Research

Figure 7:
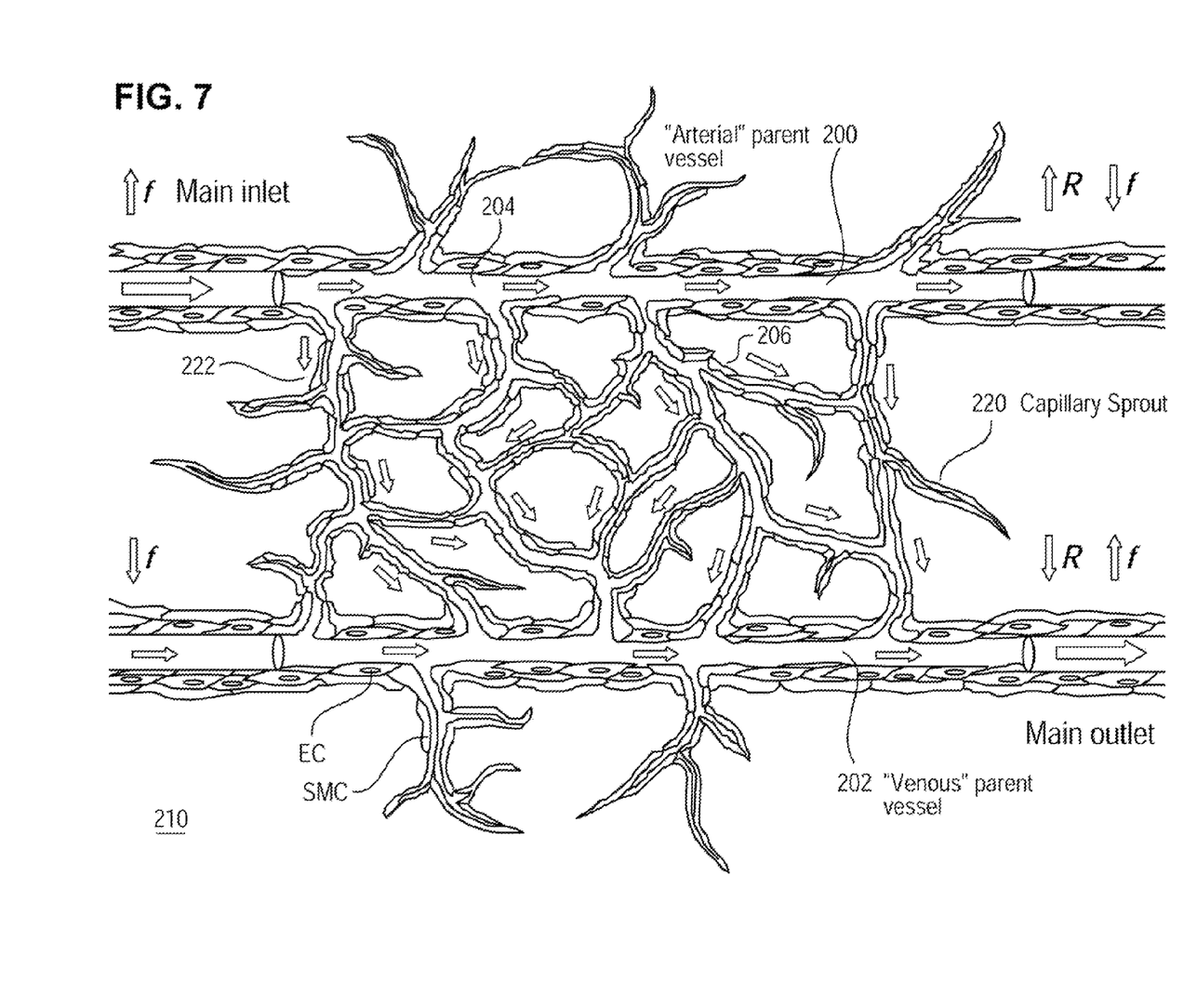
FIG. 7 shows a schematic of a capillary network between two bioartificial parent vessels in accordance with the method of the invention.

Referring now to FIG. 7, FIG. 7 shows a schematic of a capillary network between two bioartificial parent vessels 200, 202 in accordance with the method of the invention. The fluid perfusate 204 is rerouted through the capillaries 206 by decreasing the flow (f) into the "venous" parent vessel 202, and increasing the resistance (R) in the "arterial" parent vessel 200. Consequently, the perfusate 204 is driven from the vessel with higher pressure to the vessel with lower pressure, simulating natural blood flow from the arterial end to the venous end of the capillary bed.

The mandrel method may be also used for the development of models for angiogenesis research, as needed for pharmaceutical testing and research in wound repair, aging, and diseases like cancer, diabetes, arthritis, and psoriasis. Using endothelial cells only, or combinations of endothelial cells, smooth muscle cells, and pericytes, parent bioartificial microvessels (BMVs) can be cultured around micron-diameter mandrels, and embedded into a supportive gel of extracellular matrix. The mandrels will then be extracted, leaving behind patent endothelial cell tubes within the extracellular matrix gel 210 (collagen gel, basement-membrane matrices (BMMs), or others). The extraction may be done by hand, or by aid of an automated device, and with speeds varying from extremely slow to extremely fast. Other variations may include the extraction of the mandrel from bioartificial microvessels in a frozen state, coating of the mandrels with a thermo-responsive polymer, or pulling on either end of the mandrel, and thereby thinning it until rupture.

The sprouting of the parent vessels into the surrounding gel 210 will be induced by compounds, such as basic fibroblast growth factor (bFGF), vascular endothelial growth factor (VEGF), and phorbol 12-myristate-13-acetate (PMA), which are added to the gel and/or perfusate (e.g. growth medium).

Complex capillary networks 222 may be created by establishing a pressure difference between two adjacent parent bioartificial microvessels, thereby imitating arterial and venous blood flow. The fluid flow will then be re-directed from the "arterial" bioartificial microvessel through the interconnected sprouts into the "venous" bioartificial microvessel.

The perfusate may advantageously comprise oxygenated cell growth medium, free of serum and angiogenic or angiostatic substances. In another example the perfusate may be an oxygenated cell growth medium, supplemented with serum, and/or angiogenesis influencing compounds. In yet another example embodiment the perfusate may be an oxygenated physiological salt solution. In another example the perfusate may include oxygenated blood, blood components, or blood substitutes. In yet another example embodiment the perfusate may not be an oxygenated, and oxygenation of the system is achieved by diffusion through the matrix. In yet another example embodiment angiogenic or angiostatic compounds may be added to a perfusate.

In one example embodiment, angiogenic and angiostatic compounds or the like are added to the matrix. In yet another example embodiment cells comprise genetically modified cells that release products into a perfusate or into the matrix. In yet another example embodiment the matrix may advantageously comprise fibrin, collagen, and gelatin. One type of useful matrix is Matrigel® gel. In another example embodiment the matrix may comprise agar, agarose, alginate, or silica gel.

In one example embodiment, the cells may be selected from the group consisting of endothelial cells, smooth muscle cells, pericytes, human cells, animal cells, plant cells, stem cells and genetically modified cells. The matrix may be populated with cells selected from the group consisting of human cells, animal cells, and plant cells, either dispersed throughout the matrix, or locally concentrated. In some cases a fragment of healthy or diseased tissue, such as cancer tissue is embedded into the matrix.

Sprouting from parent vessels may be microscopically studied in vitro, in sectioned material or in whole-mount preparations. Perfusion of the bioartificial microvessels with fluorescent solutions (e.g. fluorescent dextrans) aids analysis of the sprout diameter, the patency of sprout lumens, and the degree of anastomization. 3D reconstruction of sprout morphologies may be performed by z-axis stacking of epifluorescence images taken by a confocal microscope. The synthesis of a pericellular basement-membrane matrix by sprouts 220 may be monitored in whole mounts and in histological (paraffin) sections by immunolabeling with anti-laminin and type IV collagen primary antibodies and fluorescent or peroxidase-tagged second antibodies.

In composite EC/SMC sprouts, the spatial relationships between the two cell types may be examined by labeling endothelial cells with a FITC-monoclonal antibody (MAb) to human CD31 (clone P2B1—Chemicon) or FITC-UEA 1 agglutinin—a specific marker for human endothelial cells smooth muscle cells may be labeled with a MAb to human alpha-SM actin followed by RITC-anti-mouse second antibodies. Details of luminal structure and interaction between endothelial cells and smooth muscle cells may be obtained from paraffin sections labeled with the aforementioned reagents.

The described fabrication methods are the foundation for commercial mass-production of angiogenesis devices with a high repeatability. With suitable preservation (e.g. cryostorage), pre-grown parent vessels or whole capillary networks could be made available to researchers in off-the-shelf fashion.

Coronary-Artery Substitutes

For the creation of coronary-artery substitutes, mandrels with an outer diameter selected to yield a coronary artery substitute having a vessel lumen with an inner diameter of approximately 4 mm to 5.5 mm. Alternatively, the mandrel may be a hollow tube that is perfused and permeable enough to allow for exchange of nutrients and gases during the growth period of the coronary-artery substitute. The coronary-artery substitutes may be grown either solely from smooth muscle cells, thus presenting a structure analog to the media layer in blood vessels, or made as composite structures from two or three cell types.

Smooth muscle cells are seeded onto the mandrels and grown to circular layers of 300-400 µm. In order to speed up the creation of coronary-artery substitutes, the SMC-phenotype may be manipulated in such way that the cells are brought into a highly proliferative phenotype during the initial growth phase, and then switched to a differentiated state after the vessel wall has reached the desired thickness. The phenotype switch will cause the smooth muscle cell's to dramatically slow down their growth rate, and induce the production of extracellular matrix proteins, such as collagen and elastin which are essential for the right mechanical properties of the vessels. The phenotype switch may be achieved by controlling the expression of certain genes. For example, with aid of a tetracycline-responsive promoter, gene expression (e.g. for elastin) may be suppressed until the vessel wall has reached the desired thickness. Omitting tetracycline from the growth medium will then activate the inserted gene. Overexpression of elastin, for instance, will inhibit further cell proliferation and exert structural and signaling functions within the vessel wail. Mechanical conditioning e.g. pulsatile flow may be used to strengthen the coronary-artery substitutes, and induce physiological alignment of the cells. Other external or internal "phenotype switches" may be potentially used, as well.

Endothelial cells may be seeded into the SMC sleeves either directly after removal of the mandrel, or after the conditioning and restructuring of the smooth muscle cells. Endothelial cell seeding may be done by infusion of an endothelial cell suspension into the SMC sleeve. The flow is then stopped for a period of time to allow proper attachment of the endothelial cells. If necessary, the vessels may be rotated, or repeatedly flipped upside down in order to facilitate an even distribution of the endothelial cells.

Alternatively, endothelial cells may be seeded onto the mandrel first. In that case smooth muscle cells are seeded onto a confluent endothelial cell layer. For this method, it will be necessary to prevent the endothelial cells from migration towards the periphery of the coronary-artery substitute, which is richer in oxygen and nutrients.

If desired, seeding fibroblast cells onto the outside of the SMC sleeves can create an adventitial layer.

The cells for creating coronary-artery substitutes may be derived from autologous, heterologous, or xenogeneic material. The cells may be stem cells, precursor cells, or differentiated cells. The cells may be genetically modified to achieve a specific phenotype or to lower the immune response of the host organism.

The method of the present invention provides the option for mass-producing off-the-shelf vessel substitutes, or vessel substitutes that are custom designed for the recipient. The method of the present invention is also suitable for the development of models for tissue engineering of coronary-artery substitutes, for research in atherogenesis, arteriogenesis, for research in the interaction of different vascular cell types with each other and with extracellular matrix components, for studies on the effects of nitric oxide, and for the study of varies pharmaceuticals.

Blood and Lymphatic Vessels of Different Size or Type

The method of the present invention may be used to create blood vessels in diameter and type other than coronary arteries. Changing the diameter of the mandrel will vary the vessel diameter. The type of the vessel (arterial, venous, lymphatic) may be varied with the phenotype of the cells, and/or the time point when the proliferation of the cells is inhibited. Veins, for example, contain only a small smooth muscle cell layer.

Other Tubular-Like Tissues

The method of the present invention may be used for the engineering of other tubular tissues, such as bile duct, lacrimal duct, pharyngotympany tube, oviduct, vas deferens, ureter, urethra etc. The method of the present invention may prove useful for the generation of nerve conduits from different cell types, including glial cells, for guidance of neural growth and repair.

BAV Systems for Engineered Tissues

The method of the present invention may be used for the engineering of tissues and organs by using arrays of removable mandrels as scaffold. The cells of the desired tissue/organ (muscle, liver, kidney, lung, skin, etc.) are seeded onto the attachment-protein coated mandrels. These mandrels may be made from solid fibers or wires, or, alternatively from perfusable permeable tubes, such cellulose. The mandrels are separated from each other in a precise spacing that allows the single cell sleeves to merge. With this method, sheets or blocks of tissue may be formed. The mandrels are then extracted (or differently removed), and the bioartificial tissue is internally perfused by aid of a perfusion system.

Wound Healing Device

Pre-manufactured bioartificial vessel systems may be used to assist in wound healing, such as for chronic ulcers in diabetic patients. Bioartificial capillary networks could be embedded into patches of supportive materials (e.g. from extracellular matrix gels, enriched with angiogenic growth factors), and placed onto the wound. Autonomously perfused with oxygenized nutrient solutions, the bioartificial vessel would facilitate the sprouting of the donor vasculature and skin. Alternatively, such a bioartificial vessel patch could be sandwiched between the wound and a skin graft, and facilitate the in-growth of the graft.

Gene-Therapy Device

Bioartificial vessels could be used for implantable drug delivery devices. Cells, taken from a patient, could be genetically modified in vitro to produce a certain protein (hormone, enzyme etc.). These cells may be then grown into bioartificial vessels or vascular networks, using the aforementioned method. Re-implanted into the host, the cells continue to produce the target substance and release it locally or systemically.

Artificial Tissues and Organs

Tissue engineered vascular networks, as described above, may be used for the creation of tissues, or even whole organs. One approach is the creation of one or more in vitro perfused parent vessels, Stroma cells from the desired tissue or organ are seeded around the parent vessels, as for example, in a gel. The stroma cells are supplied with nutrients and oxygen via the parent vessels. When the stroma cells multiply, the demand for nutrients and oxygen increases. The cells release angiogenic factors, and stimulate the vessels to sprout. The vessel system sprouts in the same rate, as the tissue grows -very similar to the natural growth. Therefore, this system would be also a good model for studies in developmental biology.

Another approach utilizes parallel arrays of mandrels as a scaffold for stroma cells. As the stroma cells multiply, cell layers are formed around the mandrels. Eventually the space between all the mandrels is filled with stroma cells, resulting in a sheet of tissue. Upon removal of the mandrels, the tissue may be perfused through the channels, left behind by the mandrels. Those channels can become endothelialized through luminal seeding. The approach is not limited to 2D. Either several sheets may be stacked, or 3D scaffolds may be used. The inventor herein has used 2D arrays as well as 3D arrays for the engineering of muscle tissue.

In yet another approach, layers of tissue and layers of vascular networks could be created independently, and then intermittently stacked. All these approaches can produce either simple models with one or two cell types, or rather complex constructs composed of several cell types.

Upon implantation, the tissues or organs engineered with these methods could be either connected directly to the blood stream, or kept perused by a perfusion system until the host vasculature has grown into the graft.

Example of Perfused Tissue Engineered Muscle Construct

Figure 8A:
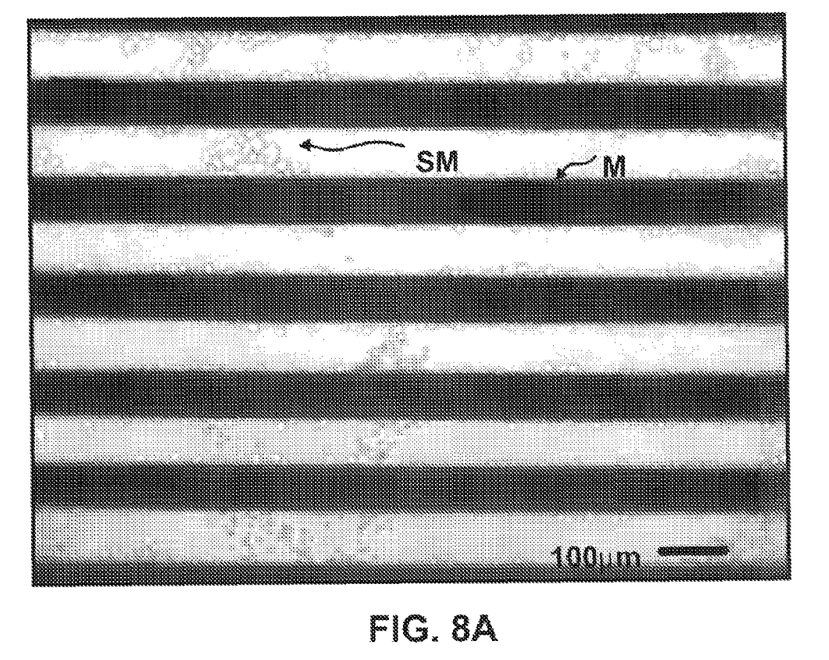
FIG. 8A shows an in vitro image of an example of a plurality of mandrels after seeding with smooth muscle cells in accordance with the method of the invention.

Referring now to FIG. 8A, an in vitro image of an example of a plurality of mandrels after seeding with smooth muscle cells in accordance with the method of the invention is shown. A plurality of mandrel-and-shrink tubing units M were sandwiched on a Mylar® frame. The distance between the mandrels M was adjusted to approximately 100 µm. The ends of all shrink tubing segments were combined in one upstream and one downstream manifold (not shown). The Mylar frame was sterilized, laminin coated and seeded with a suspension of $5 \times 10^6$ rat aortic smooth muscle cells SM (RASMCs)/ml. The cells SM attached to each individual mandrel M and multiplied, thus forming circular layers. After 10 days, the individual layers had merged and resulted in one thick sheet or plate of smooth muscle cells. After additional 7 days in growth medium, the medium was supplemented with 50 U/ml heparin for another 7 days. Then, all mandrels were extracted, and the tissue perfused with heparin-medium at a rate of 10 ml/day. The perfusion chamber was kept fixed to the bottom of a 100-mm Petri dish filled with heparin-medium. The SMC plate was perfused for 11 days, Over that time, the channels CH remained functional and remained clearly visible in vitro (as best shown in FIG. 8B).

Figure 8B:
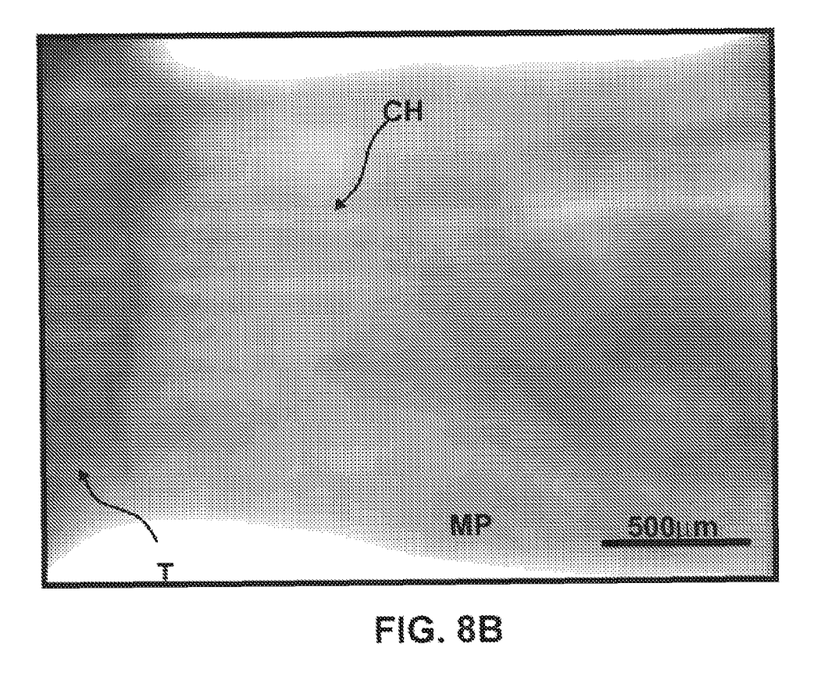
FIG. 8B shows an example of a perfused muscle plate made in accordance with the method of the invention.

Referring now to FIG. 8B, an example of a perfused muscle plate MP made in accordance with the method of the invention is shown. Fluid is shown perfused through the tubing ends (T) into channels (CH) left behind by the extracted mandrels.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

The complete disclosures of all references cited in this specification are hereby incorporated by reference. In the event of an otherwise irreconcilable conflict, however, the present specification shall control.

References

Akhtar N, Dickerson E B, Auerbach R. 2002. The sponge/Matrigel angiogenesis assay. Angiogenesis 5:75-80.

Algire G H, Chalkley H W, Legallais F Y, Park H D. 1945. Vascular reactions of normal and malignant tissues in vivo. I. Vascular reactions of mice to wounds and to normal and neoplastic transplants. J Natl Cancer Inst 6:73-85.

Andrade S P, Machado R D, Teixeira A S, Belo A V, Tarso A M, Beraldo W T. 1997. Sponge-induced angiogenesis in mice and the pharmacological reactivity of the neovascular quantitated by a fluorimetric method. Microvasc Res 54:253-261.

Arthur W T, Vernon R B, Sage E H, Reed M J. 1998. Growth factors reverse the impaired sprouting of microvessels from aged mice. Microvasc Res 55:260-270.

Ausprunk D H, Knighton D R, Folkman J. 1974. Differentiation of vascular endothelium in the chick chorioallantois: a structural and autoradiographic study. Dev Biol 38:237-248.

Clark E R, Clark E L. 1939. Microscopic observations on the growth of blood capillaries in the living mammal. Am J Anat 64:251-301.

Davis G E, Camarillo C W. 1996. An alpha 2 beta 1 integrin-dependent pinocytic mechanism involving intracellular vacuole formation and coalescence regulates capillary lumen and tube formation in three-dimensional collagen matrix. Exp Cell Res 224:39-51.

Elsdale T, Bard J. 1972. Collagen substrata for studies on cell behavior. J Cell Biol 54:626-637.

Feder J, Marasa J C, Olander J V. 1983. The formation of capillary-like tubes by calf aortic endothelial cells grown in vitro. J Cell Physiol 116:1-6.

Fishman J A, Ryan G B, Karnovsky M J. 1975. Endothelial regeneration in the rat carotid artery and the significance of endothelial denudation in the pathogenesis of myointimal thickening. Lab Invest 32:339-351.

Folkman J, Haudenschild C. 1980. Angiogenesis in vitro. Nature 288:551-556.

Folkman J, Haudenschild C C, Zetter B R. 1979. Long-term culture of capillary endothelial cells. Proc Natl Acad Sci USA 76:5217-5221.

Gimbrone M A, Jr. 1976. Culture of vascular endothelium. In: Prog Hemost Thromb. p 1-28.

Gimbrone M A, Jr., Cotran R S, Folkman J. 1974 a. Human vascular endothelial cells in culture. Growth and DNA synthesis. J Cell Biol 60:673–684.

Gimbrone M A, Jr., Cotran R S, Leapman S B, Folkman J. 1974b. Tumor growth and neovascularization: an experimental model using the rabbit cornea, J Natl Cancer Inst 52:413-427.

Greenblatt M. Shubi P. 1968. Tumor angiogenesis: transfilter diffusion studies in the hamster by the transparent chamber technique. J Natl Cancer Inst 41:111-124.

Hoying J B, Boswell C A, Williams S K. 1996. Angiogenic potential of microvessel fragments established in three-dimensional collagen gels. In vitro Cell Dev Biol Anim 32:409-419.

Jaffe E A, Nachman R L, Becker C G, Minick C R, 1973. Culture of human endothelial cells derived from umbilical veins. Identification by morphologic and immunologic criteria J Clin Invest 52:2745-2756.

Jozaki K, Marucha P T, Despins A W, Kreutzer D L. 1990. An in vitro model of cell migration: evaluation of vascular endothelial cell migration. Anal Biochem 190:39–47.

Koike T, Vernon R B, Gooden M D, Sadoun E, Reed M J. 2003. Inhibited angiogenesis in a aging: a role for TIMP-2. J Gerontol A Biol Sci Med Sci 58:B798–805.

Kubota Y, Kleinman H K, Martin G R, Lawley T J. 1988. Role of laminin and basement membrane in the morphological differentiation of human endothelial cells into capillary-like structures. J Cell Biol 107:1589–1598.

Kuzuya M. Kinsella J L. 1994. Induction of endothelial cell differentiation in vitro by fibroblast-derived soluble factors. Exp Cell Res 215:310-318.

Maciag T, Kadish J, Wilkins L, Stemerman M B, Weinstein R. 1982. Organizational behavior of human umbilical vein endothelial cells. J Cell Biol 94:511-520.

Madri J A. 1982. Endothelial cell-matrix interactions in hemostasis. Prog Hemost Thromb 6:1~24.

Madri J A, Pratt B M. 1986. Endothelial cell-matrix interactions: in vitro models of angiogenesis. J Histochem Cytochem 34:85-91.

Madri J A, Pratt B M, Tucker A M. 1988. Phenotypic modulation of endothelial cells by transforming growth factor-beta depends upon the composition and organization of the extracellular matrix. J Cell Biol 106:1375-1384.

Madri J A, Stenn K S. 1982. Aortic endothelial cell migration. I. Matrix requirements and composition. Am. J Pathol 106: 180~186.

Manoussaki D. Lubkin S R, Vernon R B, Murray J D. 1996. A mechanical model for the formation of vascular networks in vitro. Acta Biotheor 44:271~282.

Marx M, Perlmutter R A, Madri J A. 1994. Modulation of platelet-derived growth factor receptor expression in microvascular endothelial cells during in vitro angiogenesis. J Clin Invest 93:131~139.

Merwin J R, Anderson J M, Kocher O, Van Itallie C M, Madri J A, 1990. Transforming growth factor beta 1 modulates extracellular matrix organization and cell-cell junctional complex formation during in vitro angiogenesis. J Cell Physiol 142:117~128.

Montesano R. Orci L. 1985. Tumor-promoting phorbol esters induce angiogenesis in vitro. Cell 42-469~477.

Montesano R. Orci L, Vassalli P. 1983. In vitro rapid organization of endothelial cells into capillary like networks is promoted by collagen matrices. J Cell Biol 97:1648-1652.

Montesano R, Pepper M S, Orci L. 1993. Paracrine induction of angiogenesis in vitro by Swiss 3T3 fibroblasts. J Cell Sci 105 (Pt 4):1013-1024.

Mori M, Sadahira Y, Kawasaki S, Hayashi T, Notohara K, Awai. M. 1988. Capillary growth from reversed rat aortic segments cultured in collagen gel. Acta Pathol Jpn 38:1503~1512.

Nehls V, Drenckhahn D. 1995. A novel, microcarrier-based in vitro assay for rapid and reliable quantification of three-dimensional cell migration and angiogenesis. Microvasc Res 50:311-322.

Nehls V, Herrmann R. 1996. The configuration of fibrin clots determines capillary morphogenesis and endothelial cell migration. Microvasc Res 51:347-364.

Neumann T, Nicholson B S, Sanders J E. 2003. Tissue engineering of perfused microvessels. Microvasc Res 66:59-67.

Nicosia R F, Bonanno E, Smith M, Yurchenco P. 1994a. Modulation of angiogenesis in vitro by laminin~entactin complex. Dev Biol 164:197~206.

Nicosia R F, Bonanno E, Villaschi S. 1992. Large-vessel endothelium switches to a microvascular phenotype during angiogenesis in collagen gel culture of rat aorta. Atherosclerosis 95:191~199.

Nicosia R F, Nicosia S V, Smith M. 1994b. Vascular endothelial growth factor, platelet-derived growth factor and insulin-like growth factor-1 promote rat aortic angiogenesis in vitro. Am J Pathol 145:1023~1029.

Nicosia R F, Ottinetti A. 1990. Modulation of microvascular growth and morphogenesis by reconstituted basement membrane gel in three-dimensional cultures of rat aorta: a comparative study of angiogenesis in matrigel, collagen, fibrin, and plasma clot. In Vitro Cell Dev Biol 26:119-128.

Nicosia R F, Tchao R, Leighton J. 1982. Histotypic angiogenesis in vitro: light microscopic, ultrastructural, and radioautographic studies. In Vitro 18:538~549.

Nicosia R F, Tchao R, Leighton J. 1983. Angiogenesis~dependent tumor spread in reinforced fibrin clot culture. Cancer Res 43:2159~2166.

Nicosia R F, Tuszynski G P. 1994. Matrix-bound thrombospondin promotes angiogenesis in vitro. J Cell Biol 124: 183~193.

Passaniti A, Taylor R M, Pili R, Guo Y. Long P V, Haney J A, Pauly R R, Grant D S, Martin G R. 1992. A simple, quantitative method for assessing angiogenesis and antiangiogenic agents using reconstituted basement membrane, heparin, and fibroblast growth factor. Lab Invest 67:519~528.

Pepper M S, Montesano R, Vassalli J D, Orci L. 1991. Chondrocytes inhibit endothelial sprout formation in vitro: evidence for involvement of a transforming growth factor-beta. J Cell Physiol 146:170-179.

Rosen E M, Meromsky L, Setter E, Vinter D W, Goldberg I D. 1990. Quantitation of cytokine-stimulated migration of endothelium and epithelium by a new assay using microcarrier beads. Exp Cell Res 186:22~31.

Sage E H, Vernon R B. 1994. Regulation of angiogenesis by extracellular matrix: the growth and the glue. J Hypertens Suppl 12:S145~152.

Vernon R B, Angello J C, Iruela-Arispe M L, Lane T F, Sage E H. 1992. Reorganization of basement membrane matrices by cellular traction promotes the formation of cellular networks in vitro. Lab Invest 66:536-547.

Vernon R B, Gooden M D. 2002. New technologies in vitro for analysis of cell movement on or within collagen gels. Matrix Biol 21:661-669.

Vernon R B, Lara S L, Drake C J, Iruela-Arispe M L, Angello J C, Little C D, Wight T N, Sage E H. 1995. Organized type I collagen influences endothelial patterns during "spontaneous angiogenesis in vitro": planar cultures as models of vascular development. In Vitro Cell Dev Biol Anim 31:120-131.

Vernon R B, Page E H, 1999. A novel, quantitative model for study of endothelial cell migration and sprout formation within three-dimensional collagen matrices. Microvasc Res 57:118~133.

Villaschi S, Nicosia R F. 1993. Angiogenic role of endogenous basic fibroblast growth factor released by rat aorta after injury. Am J Pathol 143:181~190.

What is claimed is:

1. A method for creating networks of perfusable microvessels in vitro, said method comprising the steps of:
    first creating at least one parent vessel in vitro by attaching endothelial cells to at least one mandrel;
    next embedding the at least one mandrel with the at least one parent vessel into a matrix, such that endothelial cells of the at least one parent vessel are in direct contact with the matrix;
    next extracting the at least one mandrel from the matrix, whereby the at least one parent vessel remains embedded within the matrix;
    next perfusing the at least one parent vessel within the matrix;
    next adding stimuli to cause the at least one parent vessel to form sprouts in the matrix; and
    next subjecting the at least one parent vessel and sprouts to luminal perfusion, thereby forming a network of perfusable microvessels.

2. The method of claim 1, wherein the step of creating at least one parent vessel comprises creating two parent vessels; and wherein sprouts derived from each parent vessel anastomize to form the microvessel network.

3. The method of claim 1, wherein the step of creating at least one parent vessel comprises creating three-dimensional arrays of parent vessels.

4. The method of claim 1, wherein the step of subjecting the at least one parent vessel and sprouts to luminal perfusion includes perfusing with a perfusate that is supplemented with at least one of serum and angiogenesis influencing compounds.

5. The method of claim 1, wherein the step of subjecting the at least one parent vessel and sprouts to luminal perfusion includes perfusing with an oxygenated physiological salt solution.

6. The method of claim 1, wherein the step of subjecting the at least one parent vessel and sprouts to luminal perfusion includes perfusing with a perfusate selected from the group consisting of oxygenated blood, blood components, and blood substitutes.

7. The method of claim 1, wherein the step of subjecting the at least one parent vessel and sprouts to luminal perfusion includes diffusing oxygen through the matrix.

8. The method of claim 1, wherein the step of subjecting the at least one parent vessel and sprouts to luminal perfusion includes adding at least one of angiogenic and angiostatic compounds to the perfusate and perfusing the at least one parent vessel with the perfusate comprising the at least one of angiogenic and angiostatic compounds.

9. The method of claim 1 wherein the cells present in the parent vessel and sprouts release at least one of angiogenic and angiostatic factors into the perfusate.

10. The method of claim 1, wherein the endothelial cells comprise genetically modified endothelial cells that release at least one of angiogenic and angiostatic products into the perfusate or into the matrix.

11. The method of claim 1, wherein the matrix comprises material selected from the group consisting of fibrin, collagen, gelatin, gelled basement membrane, agar, agarose, alginate, basement membrane proteins, silica gel and combinations thereof.

12. The method of claim 1, further comprising adding at least one of angiogenic and angiostatic compounds to the matrix.

13. The method of claim 1 further comprising depositing into the matrix cells chosen from the group consisting of human cells, animal cells, smooth muscle cells, fibroblast cells, pericytes, precursor cells, stem cells, and genetically modified cells.

14. The method of claim 1, wherein the matrix is populated with cells selected from the group consisting of human cells and animal cells.

15. The method of claim 1, wherein at least one of a fragment of healthy or diseased tissue is embedded into the matrix.

16. The method of claim 1, wherein a fragment of cancer tissue is embedded into the matrix.

17. The method of claim 1 wherein the microvessel network comprises at least one microvessel selected from the group consisting of a bioartificial microvessel and a patent endothelial cell tube.

18. The method of claim 1 wherein the perfusate is re-routed through the microvessel network by decreasing the flow into a first parent vessel, and increasing the resistance in a second parent vessel so that the perfusate is driven from the second parent vessel with higher fluid pressure to the first parent vessel with lower fluid pressure.

* * * * *

UNITED STATES PATENT AND TRADEMARK OFFICE
CERTIFICATE OF CORRECTION

PATENT NO. : 7,622,298 B2  Page 1 of 1
APPLICATION NO. : 11/388920
DATED : November 24, 2009
INVENTOR(S) : Neumann It is certified that error appears in the above-identified patent and that said Letters Patent is hereby corrected as shown below:

Col. 6, Line 9: Change "FIG. 10" to --FIG. 1C--.
Col. 7, Line 8: Change "shrink-lubing" to --shrink-tubing--.

Signed and Sealed this

Thirtieth Day of March, 2010

David J. Kappos
*Director of the United States Patent and Trademark Office*